(12) United States Patent
Lassus et al.

(10) Patent No.: US 10,232,061 B1
(45) Date of Patent: Mar. 19, 2019

(54) FREEZE-DRIED FORMULATION FOR GAS-FILLED MICROVESICLES

(71) Applicant: Bracco Suisse SA, Manno (CH)

(72) Inventors: Anne Lassus, Veyrier (CH); Stéphane Gorgerat, Essertines-sur-Rolle (CH); Feng Yan, Grand Lancy (CH); Christian Guillot, Beaumont (FR); Jean Brochot, Cruseilles (FR)

(73) Assignee: Bracco Suisse SA, Manno (CH)

( * ) Notice: Subject to any disclaimer, the term of this patent is extended or adjusted under 35 U.S.C. 154(b) by 0 days.

(21) Appl. No.: 16/028,536

(22) Filed: Jul. 6, 2018

(51) Int. Cl.
*A61K 49/22* (2006.01)

(52) U.S. Cl.
CPC .................................. *A61K 49/223* (2013.01)

(58) Field of Classification Search
CPC .................................................. A61K 49/223
See application file for complete search history.

(56) References Cited

U.S. PATENT DOCUMENTS 5,686,060 A    11/1997   Schneider et al.

FOREIGN PATENT DOCUMENTS

WO          94/09829 A1     5/1994

OTHER PUBLICATIONS

European Medicines Agency, Assessment report, Sonovue, May 2, 2014, http://www.ema.europa.eu/docs/en_GB/document_library/EPAR_-_Assessment_Report_-_Variation/human/000303/WC500170218.pdf (Year: 2014).*
Gines, J.M., et al. "Thermal characterization of polyethylene glycols applied in the pharmaceutical technology using differential scanning calorimetry and hot stage microscopy," Journal of Thermal Analysis, 46:291-304 (1996).
Package insert of LUMASON (sulfur hexafluoride lipid-type A microspheres), Bracco Diagnostics Inc. (2016).

* cited by examiner

*Primary Examiner* — Michael G. Hartley
*Assistant Examiner* — Leah H Schlientz
(74) *Attorney, Agent, or Firm* — VIVICAR Law, PLLC

(57) ABSTRACT

A freeze-dried powder composition comprising a phospholipid and a polyethylene glycol, said polyethylene glycol having a percentage of folded polymeric chains of 40% or higher. The composition is suitable for preparing gas-filled microvesicles.

24 Claims, 3 Drawing Sheets

FREEZE-DRIED FORMULATION FOR GAS-FILLED MICROVESICLES

TECHNICAL FIELD

The invention relates to a formulation for preparing gas-filled microvesicles for use in ultrasound contrast imaging.

BACKGROUND OF THE INVENTION

Rapid development of contrast agents In the recent years has generated a number of different compositions and formulations, which are useful in contrast-enhanced imaging of organs and tissues of human or animal body as well as in therapeutic treatments thereof.

A class of contrast agents particularly useful for Contrast Enhanced UltraSound imaging ("CEUS" Imaging) includes suspensions of gas bubbles of nano- and/or micro-metric size dispersed in an aqueous medium. The gas is typically entrapped or encapsulated in a film-layer comprising, for instance, emulsifiers, oils, thickeners or sugars. These stabilized gas bubbles (dispersed in a suitable physiological solution) are generally referred to in the art with various terminologies, depending typically from the stabilizing material employed for their preparation; these terms include, for instance, "microspheres", "microbubbies", "microcapsules" or "microballoons", globally referred to here as "gas-filled microvesicles" (or "microvesicles").

UltraSound Contrast Agents ("USCA"s) are manufactured according to various manufacturing methods. One of these methods, see e.g. WO 94/09829([1]), entails the dissolution of a mixture of film-forming components (such as phospholipids and/or fatty acids) and of a hydrophilic stabilizing compound (e.g. polytheleneglycol) in an organic solvent; the obtained mixture is thus filled into vials which are subjected to freeze-drying (lyophilization). The vials containing a solid freeze-dried solid residue ("cake") at the bottom thereof are then filled with a suitable gas (e.g. a fluorinated gas) and finally sealed for storage. Before use, an aqueous suspension of microbubbles is easily prepared by injecting a suitable liquid into the vial (e.g. saline) and shaking the vial to dissolve the solid residue.

A commercially available USCA which can be manufactured according to the above method is SonoVue® (or Lumason® in the USA), from Bracco.

The Applicant has now observed that the polyethylene glycol employed in the preparation of the lyophilized "cake" may have variations in its characteristics which may negatively affect the number of gas-filled microvesicles obtained upon reconstitution of the lyophilized powder.

In particular, the Applicant has observed that different releases (even from a same manufacturer) of commercially available PEG4000 may have different amounts of folded polymeric chains in the polymeric material. As observed by the Applicant, if the percentage of folded chains in the polymeric material is too low, this may result in a too high number of vials failing to pass the acceptability test in a manufacturing batch. As under an industrial scale a manufacturing batch may comprise few thousand of vials, it may well be understood that even a relatively low number of discharged vials is highly undesirable.

Based on the above observation, the Applicant has determined that the polyethylene glycol used in the formulation of the lyophilized powder for the preparation of gas-filled microvesicles shall have a percentage of folded polymeric chains higher than a predetermined value.

SUMMARY OF THE INVENTION

An aspect of the invention relates to a freeze-dried powder composition for the preparation of gas-filled microvesicles, said composition comprising a phospholipid and a polyethylene glycol, wherein said polyethylene glycol has a percentage of folded polymeric chains of 40% or higher.

Preferably said percentage of folded chains is of at least 42%, more preferably of at least 44% and even more preferably of at least 48%.

In a preferred embodiment, said polyethylene glycol has an average molecular mass (or molecular weight in number, Mn) of at least 4000 g/mol (or daltons, Da), more preferably of at least 4025 g/mol and even more preferably of at least 4050 g/mol.

In another preferred embodiment said phospholipid is DSPC, DPPG-Na or (preferably) a mixture thereof.

Preferably said composition further comprises a fatty add, preferably palmitic acid.

In another aspect the present invention relates to a sealed vial containing a composition as above defined in contact with a physiologically acceptable gas.

Preferably said gas is a fluorinated gas, more preferably sulphur hexafluoride.

According to another aspect the invention relates to a suspension of gas-filled microvesicles obtained by dispersing said freeze-dried powder composition, in the presence of a gas, in a physiologically acceptable liquid, preferably in a 0.9% w/v NaCl solution.

According to a further aspect, the invention relates to a method for manufacturing a lyophillzed composition comprising a phospholipid, a polyethylene glycol and optionally a fatty acid, which comprises:
  dissolving said phospholipid, optionally said fatty acid, and said polyethylene glycol in a solvent;
  freezing the solution; and
  removing the solvent by lyophilization;
  wherein said polyethylene glycol has a percentage of folded polymeric chains of 40% or higher.

A further aspect of the invention relates to a method of ultrasound imaging which comprises:
  administering an effective amount of a suspension of gas-filled microvesicles as above defined to a patient;
  transmitting an ultrasound signal to a body part of said patient;
  collecting an echographic signal from said body part.

FIGURES

DETAILED DESCRIPTION OF THE INVENTION

Figure 1:
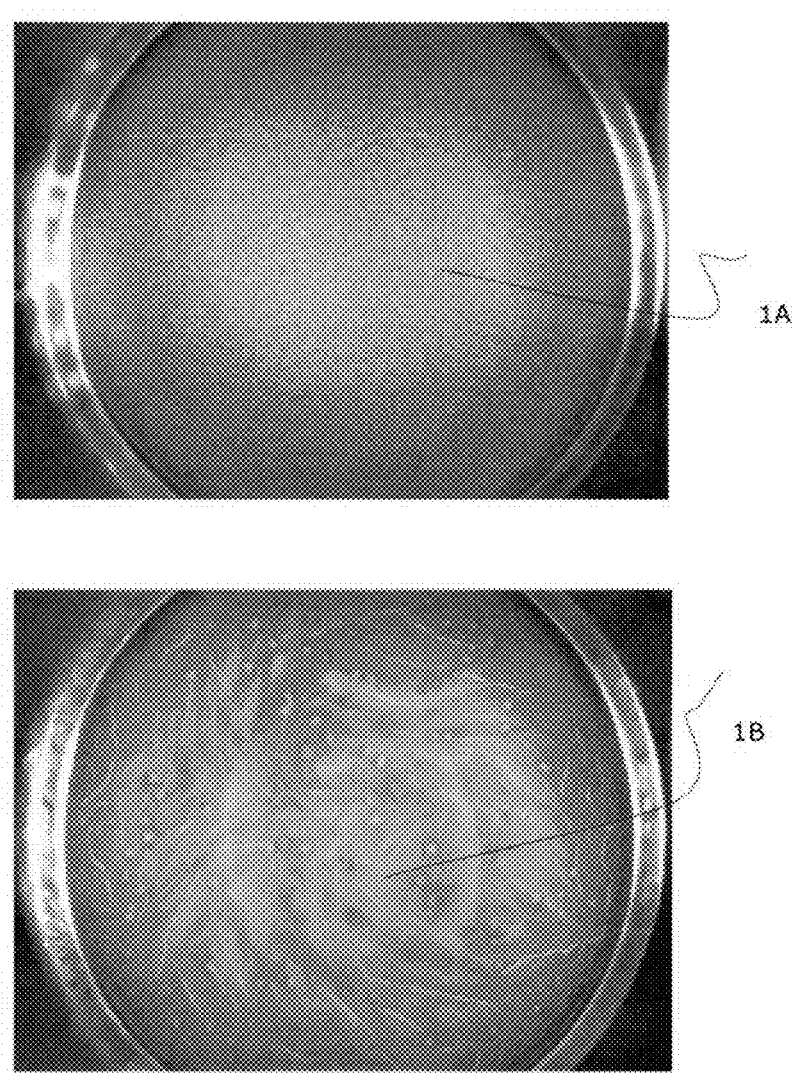
FIG. 1 shows an example of a "smooth" freeze-dried cake (1a) and of a "rough" freeze-dried cake (1b)

SonoVue® (or Lumason®) is formulated as a sterile, pyrogen-free lyophilized powder stored in a septum vial. The lyophilized powder contains polyethylene glycol 4000 (PEG4000, 24.56 mg), distearoylphosphatidyl-choline (DSPC, 0.19 mg), dlpalmitoylphosphatidylglycerol sodium (DPPG-Na 0.19 mg) and palmitic add (0.04 mg). The headspace of each vial is filled with sulfur hexafluoride ($SF_6$). Upon reconstitution with 5 mL of sterile saline, SonoVue/Lumason is a milky white, homogeneous suspension containing microvesicles (also identified as "microspheres" or "microbubbles") filled with sulfur hexafluoride.

The preparation of the lyophilized powder can be accomplished according to the procedure described in the above cited patent application WO 94/09829. Typically, the process entails the dissolution of PEG4000, phospholipids and palmitic acid, in a respective weight ratio corresponding substantially to the one in the final freeze-dried product, in a suitable solvent (e.g. dioxane, cyclohexanol, 2-methyl-2-butanol, tetrachlorodifluorethylene or tert-butanol). For instance, the solution may contain from 22 to 28 parts by weight of polyethylene glycol, from 0.15 to 0.25 parts by weight of DSPC, from 0.15 to 0.25 parts by weight of DPPG-Na and from 0.02 to 0.06 parts by weight of palmitic acid. The obtained solution is then filled into the glass vials which are rapidly frozen (e.g. at −45° C.) and then submitted to the lyophilization process. Typically, under industrial scale, each manufacturing batch comprises few thousand of vials. At the end of the freeze-drying step, the upper space of the vials containing the lyophilized residue in the form of a solid cake is saturated with $SF_6$ gas and the vial is sealed with a rubber stopper. The so obtained vials may be stored for a period of at least two years.

As observed by the Applicant, the quality of the freeze-dried cakes in the vials of a manufacturing batch may be however negatively affected by the use of a PEG having an amount of folded chains lower than a predetermined limit.

As mentioned for instance by Ginés et al.,[2] polyethylen glycols (PEGs) are semi-crystalline hydrophilic polymers containing, in the solid state, amorphous and ordered crystalline phases in varying proportions, depending on their synthesis and thermal history. In the crystalline regions, the polymeric chains exist as both extended and folded chains, particularly in PEGs with a molecular weight between about 4000 and 6000 g/mol. As observed by Ginés et al. the amount of folded chains in PEG4000 is generally higher when a molten sample is left cooling at room temperature, with respect a same molten sample which is quenched in an ice bath or by immersion in liquid nitrogen.

As observed by the Applicant, the amount of folded chains in the PEG material used as stabilizing compound (typically PEG4000) in a formulation for preparing gas-filled microvesicles may vary substantially among various commercial lots, even from a same manufacturer, for materials having the same nominal molecular weight (i.e. 4000 g/mol).

The Applicant has now unexpectedly found that if a PEG with a too low percentage of such folded polymeric chains is employed, this may have a negative impact on the quality of the freeze-dried cakes contained in the vials of a batch manufactured by using such PEG. In particular, if the percentage of folded polymeric chains in the PEG falls below a predetermined limit, the amount of rejected vials in such batch (i.e. vials with a freeze-cake not fulfilling predetermined specifications) will become excessively high.

Among the various criteria for determining the quality of a freeze-dried cake, an important one is the physical aspect of the cake. In particular, the Applicant has determined a relatively good correlation between the physical aspect of a cake and the quality of the suspension of gas-filled microvesicles produced upon reconstitution of such cake with a physiologically acceptable liquid. As observed by the Applicant, cakes showing a relatively smooth surface appearance (see e.g. FIG. 1a) provide in general higher number of microvesicles upon reconstitution, while those showing a relatively rough surface appearance (see e.g. FIG. 1b) result In a substantially lower number of microvesicles upon reconstitution. Furthermore, as observed by the Applicant, cakes with a relatively smooth surface result in microvesicles suspensions with higher MVC (Microbubbles Volume Concentration, i.e. the total amount of gas contained in the reconstituted microvesicles per mL of suspension). In general, due to the above mentioned lower quality, suspensions of gas-filled microvesicles obtained by reconstitution of rough cakes are less effective for performing CEUS imaging.

Figure 2:
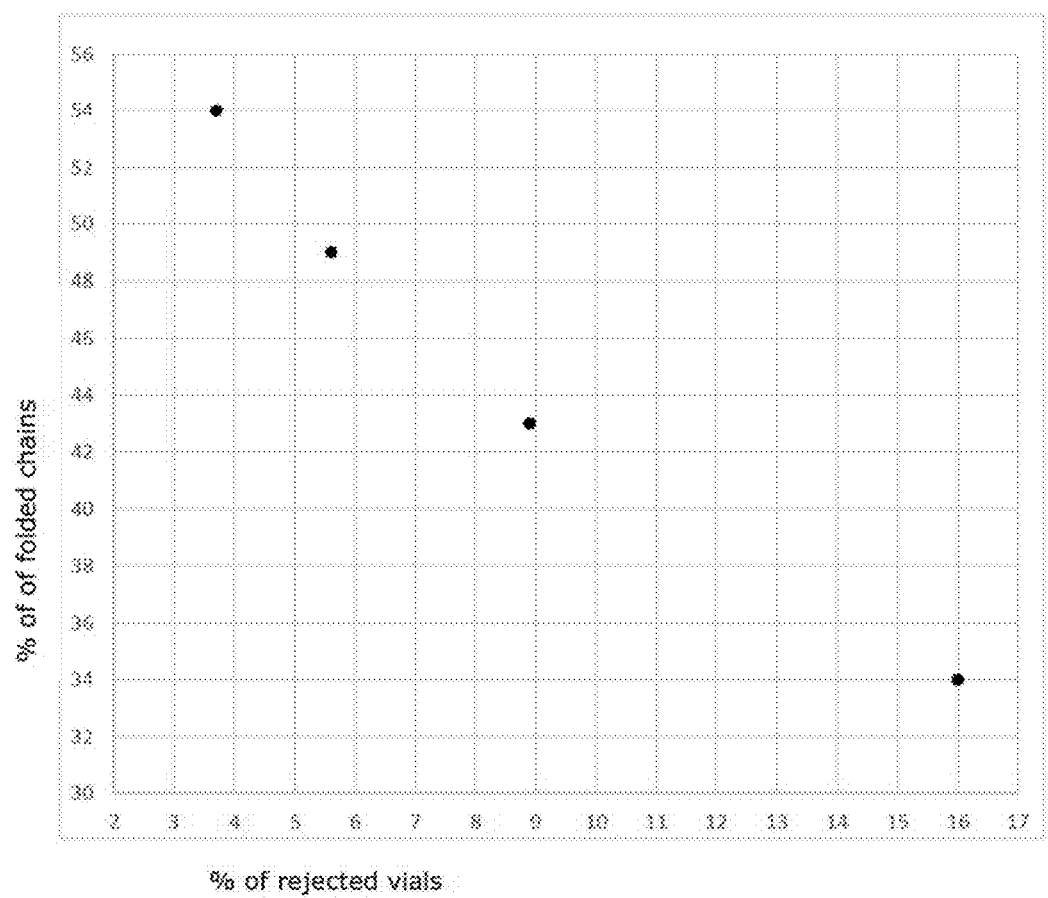
FIG. 2 is a plot illustrating the relationship between percentage of folded polymeric chains and amount of rejected vials per manufacturing batch.

In particular, as observed by the Applicant, when the percentage of folded chains falls below 40% of the total amount of polymeric chains, the amount of rejected vials (with "rough" cakes) is generally higher than 12%, as illustrated in FIG. 2 (e.g. 16% of rejects for PEG with 34% of folded chains). Thus, in order to further minimize the vials' rejection rate the Applicant has determined that the percentage of folded chains in the PEG shall preferably be of at least 42% with respect to the total amount of polymeric chains. More preferably the percentage of folded polymeric chains shall be higher than 44% and even more preferably higher than 48%. While in principle there is no upper limit for the percentage of folded chains (typically PEGs with nominal Mn of about 6000 g/mol may have a percentage of folded chains up to about 100%), PEGs with nominal Mn of about 4000 (e.g. up to 4600 g/mol) typically have a percentage of folded chains lower than 80%, typically of 75% or lower. Preferably, the percentage of folded chains is of about 70% or lower, more preferably of about 65% or lower and even more preferably of 60% or lower.

Determination of Percentage of Folded Chains

The percentage of folded chains in the polymeric material can be determined according to methods known in the arts, preferably by Differential Scanning Calorimetry (DSC). A preferred method (also used in the following examples) is Modulated Differential Scanning Calorimetry (MDSC), performed for instance by using a DSC-Q2000 system (TA instruments, New Castle, Del. USA).

The details of the MDSC method are described In the working examples.

Briefly, the sample is submitted to a heat/cool/heat cycle at a constant temperature rate (e.g. of 2° C./min) over a predetermined temperature range (e.g. from 20° C. to 70° C.) by applying a temperature modulation amplitude (e.g. 0.16° C. each 30 seconds).

Figure 3:
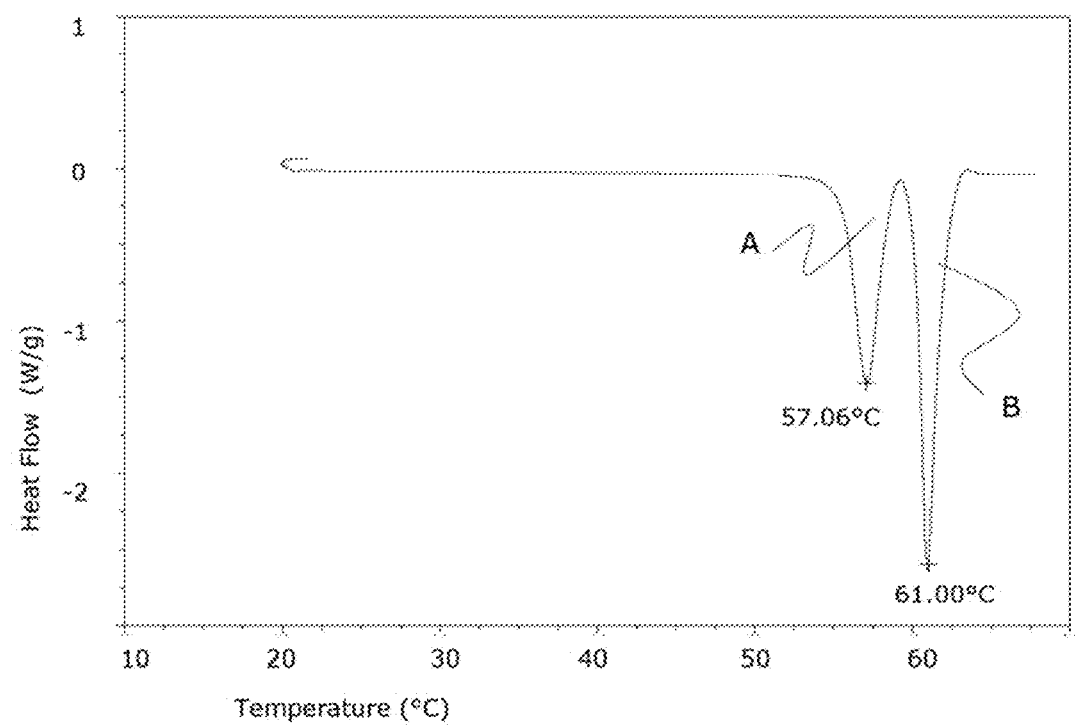
FIG. 3 shows an illustrative MDSC thermogram of the second heating cycle of a polyethylene glycol sample.

The fraction of polymeric material present in the folded form can be characterized during the second heating cycle. Indeed, polyethylene glycol has the distinctive feature to split into two peaks during the second heating cycle, the peak with the lower melting temperature corresponding to the melting of the PEG with folded chains, while the peak with the higher melting temperature corresponds to the melting of the PEG with unfolded chains. FIG. 3 shows a typical MDSC thermogram of PEG, where said first and second melting peaks obtained during said second heating cycle are identified. In particular, peak A in FIG. 3 (at about 57° C.) corresponds to the melting of PEG with folded chains, while peak B (at about 61° C.) corresponds to the melting of PEG with unfolded chains. The area of each peak corresponds to the respective fractions of PEG with folded or unfolded chains. The fraction of polymeric folded chains, f(folded), is thus determined according to following equation 1:

$$f(\text{folded}) = \frac{A_{folded}}{A_{folded} + A_{unfolded}} \quad \text{Equation 1}$$

where $A_{folded}$ and $A_{unfolded}$ represent the normalised heat flow integrals (enthalpy of melting, joule/grams of sample) for the folded and unfolded PEG forms as calculated from the areas under the respective peaks of the second heating cycle of the MDSC thermogram of the PEG sample. The percentage of folded polymeric chains in a sample of polyethylene glycol is thus: $f(\text{folded}) \times 100$.

As illustrated in the experimental part, while there is a certain correlation between percentage of folded chains and average molecular mass of the polyethylene glycol (in general, the higher the molecular mass of the polymer, the higher the percentage of folded chains), such correlation is not necessarily straight. This finding shows that while the molecular mass plays a role in the amount of folded chains, it is not necessarily the sole determinant, as the amount of folded chains may also be influenced by the thermal history of the polymeric sample (including, for instance, parameters of the manufacturing/cooling process, storage conditions or ageing of the sample). Nevertheless, the Applicant has observed that the polyethylene glycol shall preferably display an average molecular mass (or average molecular weight in number, Mn) of at least 4000 g/mol, more preferably of at least 4025 g/mol and even more preferably of at least 4050 g/mol. Particularly preferred is a polyethylene glycol with a Mn of 4075 or higher, e.g. 4100 or higher. While there is In principle no higher value of Mn for what concerns the amount of folded chains, the polymer shall however have a molecular weight compatible with the viscosity of the final suspension of gas-filled microvesicles. Thus a Mn of 6200 g/mol or lower is preferred, more preferably of 5000 g/mol or lower and even more preferably of 4400 g/mol or lower The molecular mass of polyethylene glycol can be determined according to conventional methodology, preferably by titration of the hydroxyl value (OHV), e.g. according to DIN53240 standard. The average molecular mass for PEG (or average molecular weight in number, Mn) is then easily calculated from the OHV, e.g. as follows: Mn=112220/OHV.

Determination of Cake Aspect

The check of the physical appearance of the cake can be made by visual inspection. Preferably the visual inspection is performed by using a semi-automatic inspection machine with a suitable lightning and mirror system, such as a Seidenader M10063 semi-automatic machine. In the practice, the cake is illuminated from the top with a suitable light system while the bottom of the cake is visualized by transparency on an underlying mirror. The aspect of the cake visualized on the mirror is thus checked by an operator, which determines the acceptable or rejected vials based on the following criteria. Freeze-dried cakes passing the acceptability test have a substantially smooth aspect ("smooth cakes") with a homogeneous surface with multiple crystal-like structures throughout the cake (see FIG. 1a). On the other side, cakes being rejected at the acceptability test have a substantially rough aspect ("rough cakes") with cracks and/or larger spots appearing in the cake (see e.g. FIG. 1b).

With this acceptability test, the Applicant has determined that the amount of rejected vials in a manufacturing batch is inversely proportional to the percentage of folded chains in the polyethyleneglycol employed for the preparation of the various batches, as illustrated in detail in the following examples.

When tested upon reconstitution with saline, smooth cakes generally resulted in higher amount of microbubbles in the suspension as well as in a higher volume of gas contained in the microbubbles.

The reconstituted suspension can be used for administration to a patient in conventional CEUS procedures, where the patient or a body part thereof is submitted to ultrasound insonation and the echografic signal is collected and analysed.

The following examples will help to further illustrate the invention.

EXAMPLES

Example 1

Determination of Percentage of Folded Chains by MDSC a. Equipment and Calibration of the System All MDSC experiments were carried out on DSC-Q2000 system (TA Instruments, New Castle, Del. USA) equipped with Tzero™ technology (allowing direct measurement of heat capacity) and with Modulated® option that allows overlay of a sinusoidal temperature oscillation on the traditional linear ramp.

A refrigerated cooling accessory (RCS90) with a two-stage refrigeration system for conveniently operating over the temperature range from −90° C. to 550° C. was used.

Data acquisition and processing were performed with the help of Universal Analysis Software package.

Tzero aluminum crucibles (ref 901683.901) and Tzero aluminum lid (ref 901671.901), all from TA instruments, were used to contain the sample to be measured and to seal the crucible by means of a Tzero press (ref 901600.901).

DSC system calibration including temperature and heat flow was carried out with Indium metal. In practice, a piece of indium of approximately 5 mg was weighted, pressed flat and transferred in a Tzero crucible sealed with a Tzero lid by means of a Tzero press. The calibration scanning program was run between 100° C. and 180° C. at a constant temperature rate of 10° C./min. The specifications of Indium were as follows: enthalpy of fusion and onset temperature of fusion have to be 28.71 J/g±0.5 J/g and 156.6° C.±0.25° C., respectively.

b. Preparation of the Samples and MDSC Measurements

Four different lots of PEG4000 were characterized according to the following procedure.

PEG4000 flakes of each sample were crushed into small parts by means of a pestle, and a sample mass of 5 mg±0.1 mg was weighted with a microbalance XP26 (Mettler Toledo) in Tzero crucibles, which were then sealed with a Tzero lid by means of a Tzero press. An empty Tzero crucible of similar weight compared to empty sample crucible was similarly prepared and used as a reference.

The MDSC measurement was performed on each crucible containing the PEG4000 sample by applying a heat/cool/heat cycle at a constant temperature rate of 2° C./min over a temperature range from 20° C. to 70° C. as outlined in Table 1 below. A heat only modulation signal was applied (0.16° C. temperature modulation amplitude every 30 seconds temperature modulation period). Nitrogen was used as purging gas at a flow rate of 50 mL/min.

TABLE 1

MDSC heat/cool/heat cycles

| Step # | Description |
|---|---|
| 1 | Equilibrate at 20.00° C. |
| 2 | Modulate ±0.16° C. every 30 s |
| 3 | Isothermal for 5.00 min |
| 4 | Ramp 2.00° C./min to 70.00° C. |
| 5 | Mark end of cycle 1 |
| 6 | Isothermal for 5.00 min |
| 7 | Ramp 2.00° C./min to 20.00° C. |
| 8 | Mark end of cycle 2 |
| 9 | Isothermal for 5.00 min |
| 10 | Ramp 2.00° C./min to 70.00° C. |
| 11 | Mark end of cycle 3 |
| 12 | End of method |

The following parameters were determined on the MDSC thermogram using Universal Analysis software:

The temperature at peak and the enthalpy of fusion during the first heating cycle;

The temperature at peak and the enthalpy of crystallization during the first cooling cycle;

The temperature at peak and the enthalpies of fusion of folded and extended chains during the second heating cycle.

The percentage of polymeric material present in the folded form was characterized during the second heating cycle and calculated according to Equation 1 previously illustrated.

For each lot of PEG4000, the procedure was repeated on three different samples.

Details of the measurements and results are provided in the following tables 2 to 5.

TABLE 2

MDSC main characteristics of PEG4000 Lot 1 (comparative)

| | 1$^{st}$ Heat. Run Melting Peak | | 1$^{st}$ Cool. Run Crystall. Peak | | Second heating Run Melting Peaks 1 and 2 | | | | Peak 1 |
|---|---|---|---|---|---|---|---|---|---|
| | Temp. ° C. | Heat flow J/g | Temp. ° C. | Heat flow J/g | Temp. ° C. | Heat flow J/g | Temp. ° C. | Heat flow J/g | % Folded chains |
| Lot 1a | 60.53 | 205.4 | 43.97 | 196 | 56.71 | 73.52 | 60.87 | 145.1 | 34 |
| Lot 1b | 60.63 | 199.1 | 43.23 | 219.4 | 56.89 | 70.33 | 60.97 | 139.5 | 34 |
| Lot 1c | 60.58 | 206.3 | 43.83 | 204.2 | 56.89 | 75.26 | 60.91 | 142 | 35 |

Mean % of folded chains: 34%

TABLE 3

MDSC main characteristics of PEG4000 Lot 2

| | 1$^{st}$ Heat. Run Melting Peak | | 1$^{st}$ Cool. Run Crystall. Peak | | Second heating Run Melting Peaks 1 and 2 | | | | Peak 1 |
|---|---|---|---|---|---|---|---|---|---|
| | Temp. ° C. | Heat flow J/g | Temp. ° C. | Heat flow J/g | Temp. ° C. | Heat flow J/g | Temp. ° C. | Heat flow J/g | % Folded chains |
| Lot 2a | 60.78 | 197 | 44.88 | 188.3 | 57.27 | 91.04 | 61.12 | 117.3 | 44 |
| Lot 2b | 60.77 | 197.7 | 44.8 | 187.8 | 57.31 | 89.07 | 61.19 | 118.6 | 43 |
| Lot 2c | 60.68 | 202.1 | 43.43 | 191.7 | 57.26 | 91.83 | 61.12 | 123.5 | 43 |

Mean % of folded chains: 43%

TABLE 4

MDSC main characteristics of PEG4000 Lot 3

| | 1$^{st}$ Heat. Run Melting Peak | | 1$^{st}$ Cool. Run Crystall. Peak | | Second heating Run Melting Peaks 1 and 2 | | | | Peak 1 |
|---|---|---|---|---|---|---|---|---|---|
| | Temp. ° C. | Heat flow J/g | Temp. ° C. | Heat flow J/g | Temp. ° C. | Heat flow J/g | Temp. ° C. | Heat flow J/g | % Folded chains |
| Lot 3a | 60.89 | 204.7 | 46.37 | 207.2 | 57.34 | 107.8 | 61.18 | 109.2 | 50 |
| Lot 3b | 60.93 | 197.3 | 46.27 | 194.5 | 57.35 | 101.3 | 61.2 | 105.5 | 49 |
| Lot 3c | 60.89 | 204.8 | 46.24 | 198.1 | 57.33 | 104.6 | 61.17 | 112.7 | 48 |

Mean % of folded chains: 49%

TABLE 5

MDSC main characteristics of PEG4000 Lot 4

| | 1$^{st}$ Heat. Run Melting Peak | | 1$^{st}$ Cool. Run Crystall. Peak | | Second heating Run Melting Peaks 1 and 2 | | | | Peak 1 |
|---|---|---|---|---|---|---|---|---|---|
| | Temp. °C. | Heat flow J/g | Temp. °C. | Heat flow J/g | Temp. °C. | Heat flow J/g | Temp. °C. | Heat flow J/g | % Folded chains |
| Lot 4a | 60.97 | 201.6 | 48.99 | 330.2 | 57.69 | 112 | 61.18 | 97.34 | 54 |
| Lot 4b | 60.9 | 197.5 | 49.04 | 329.1 | 57.76 | 113.9 | 61.14 | 94.79 | 55 |
| Lot 4c | 60.9 | 200.8 | 49.1 | 356 | 57.76 | 114.6 | 61.13 | 96.62 | 54 |

Mean % of folded chains: 54%

The results of the MDSC measurements for respective PEG lots are summarized in the following table 6, together with respective average molecular weights in number (Mn) as provided by the supplier.

TABLE 6

PEG4000 % of folded chains and average Mn

| PEG4000 Lot No | % Folded Chains | Mn (g/mol) |
|---|---|---|
| Lot 1 (comp) | 34 | 3997 |
| Lot 2 | 43 | 4107 |
| Lot 3 | 49 | 4159 |
| Lot 4 | 54 | 4154 |

The results reported in tables 2 to 6 show that lot 1 (with only 34% of folded polymeric chains) does not fulfill the requirements according to the invention, while the other three lots of PEG4000 do satisfy such requirements. Furthermore, it can also be observed that Lot N° 1 has a Mn lower than 4000, while all the other lots have a Mn higher than 4000 g/mol, in particular of at least 4100 g/mol.

Example 2

Preparation of Freeze-Dried Cakes

The procedure for preparing the freeze-dried cakes follows essentially the one illustrated in the working examples of WO 94/09829. Briefly, DSPC, DPPG-Na and PA in a weight ratio of 4.75/4.75/1 are first dissolved in hexane/ethanol (8/2, v/v) at a concentration of about 5 g/L and the solvents were evaporated under vacuum. The residue is admixed with PEG4000 in a weight ratio of about 0.017:1, the mixture is dissolved in tert-butanol at around 60° C. and the clear solution is used to fill respective DIN8R vials (with a corresponding volume containing about 25 mg of the mixture). The vials are then rapidly cooled at −45° C. and then subjected the final lyophilization step. At the end of the lyophilization, the ambient of the lyophilizer is saturated with SF$_6$ at atmospheric pressure and the vials (containing the solid freeze-dried cake in contact with SF$_6$) are sealed with a rubber stopper.

The above manufacturing procedure was applied by using each of the four PEG4000 lots (lot 1 to 4) characterized in Example 1, thus obtaining four batches of few thousand vials each (batches 1 to 4, respectively), each vial containing 25 mg of freeze-dried solid material in the form of a cake at the bottom of the vial.

Example 3

Vials/Cakes Check

The batches obtained according to preparation method illustrated in example 2 were checked for the presence of not-acceptable freeze-dried cakes according to the following procedure.

The vials of each batch were inspected and classified as either "acceptable vials", i.e. containing a smooth cake (SCV, e.g. as in FIG. 1a) or as "rejected vials", i.e. containing a rough cake (RCV, e.g. as in FIG. 1b), by using a Seldenader M10063 semi-automatic machine according to the procedure described before.

The results of the check performed according to the above procedure are illustrated in the following table 7 and reported in FIG. 2.

TABLE 7

Amount of rejected vials vs. % of folded chains in PEG4000

| Manufacturing Batch No | % of rejected vials | % of folded chains in PEG4000 |
|---|---|---|
| Batch 1 (comp) | 16 | 34 |
| Batch 2 | 8.9 | 43 |
| Batch 3 | 5.6 | 49 |
| Batch 4 | 3.7 | 54 |

As inferable from the results illustrated in table 7, the percentage of rejected vials in manufacturing batch N° 1 (where the PEG4000 of the composition has only 34% of folded chains) is much higher with respect to the amount of rejection of other batches manufactured with a PEG4000 having higher percentages of folded chains, according to the invention.

Example 4

Suspension of Gas-Filled Microvesicles from Reconstituted Vials

Six vials were sampled from each group of "acceptable vials" and "rejected vials" (as defined in example 3 above) to characterize the microbubbles obtained by reconstituting the cakes contained in said vials.

A Coulter Counter Multisizer 3 fitted with a 30 μm aperture tube was used to measure various parameters of the gas-filled microvesicles suspension such as the MVC (Microvesicles Volume Concentration) and the total number of microvesicles in the suspension. Briefly, 50 μL of microbubble suspension were diluted in 100 mL NaCl 0.9% solution, using an analytical volume of 100 μL.

The results of the measurements (mean values for each group of vials) are reported in table 8 below.

TABLE 8

| Characteristics of gas-filled microvesicles prepared from smooth or rough cakes | | |
|---|---|---|
| Type of vials | MVC µL/mL | Microvesicles concentration (part/mL) |
| Accepted (smooth cakes) | 6.4 | $4.38 \times 10^8$ |
| Rejected (rough cakes) | 3.2 | $3.87 \times 10^8$ |

As inferable from the results illustrated in table 8, microvesicles obtained upon reconstitution of smooth cakes show a higher volume of total gas entrapped In the microvesicles (the double in particular) as well as a higher number of microvesicles in the suspension ($0.5 \times 10^8$ in particular).

CITED DOCUMENTS

[1] International Patent Application WO 94/09829 (Bracco International)
[2] Gines et al., "Thermal Characterization Of Polyethylene Glycols Applied in the Pharmaceutical Technology Using Different Scanning Calorimetry and Hot Stage Microscopy", Journal of Thermal Analysis, Vol. 46 (1996) 291-304.

The invention claimed is:

1. A freeze-dried powder composition for the preparation of gas-filled microvesicles, said composition comprising a phospholipid and a polyethylene glycol, wherein said polyethylene glycol has a percentage of folded polymeric chains of from 40% to 80%.

2. The composition according to claim 1 wherein said percentage of folded chains is of at least 42%.

3. The composition according to claim 1 wherein said percentage of folded chains is of at least 44%.

4. The composition according to claim 1 wherein said polyethylene glycol is a PEG4000 having an average molecular weight in number (Mn) of from 4000 g/mol to 4600 g/mol.

5. The composition according to claim 4 wherein said Mn is of at least 4025 g/mol.

6. The composition according to claim 1 wherein said phospholipid is distearoylphosphatidyl-choline (DSPC), dipalmitoylphosphatidylglycerol sodium (DPPG-Na) or a mixture thereof.

7. The composition according to claim 4 wherein said phospholipid is DSPC, DPPG-Na or a mixture thereof.

8. The composition according to claim 1 wherein said composition further comprises a fatty acid.

9. The composition according to claim 8 wherein said fatty acid is palmitic acid.

10. The composition according to claim 7 further comprising palmitic acid.

11. The composition of claim 10 comprising from 22 to 28 parts by weight of PEG4000, from 0.15 to 0.25 parts by weight of DSPC, from 0.15 to 0.25 parts by weight of DPPG-Na and from 0.02 to 0.06 parts by weight of palmitic acid.

12. The composition of claim 11 comprising 24.56 mg of PEG4000, 0.19 mg of DSPC, 0.19 mg of DPPG-Na and 0.04 mg of palmitic acid.

13. A sealed vial containing a freeze-dried powder composition according to claim 1 in contact with a physiologically acceptable gas.

14. A sealed vial containing a freeze-dried powder composition according to claim 11 in contact with a physiologically acceptable gas.

15. The sealed vial according to claim 13, wherein said gas is a fluorinated gas.

16. The sealed vial according to claim 14, wherein said gas is a fluorinated gas.

17. A method for manufacturing a lyophilized composition comprising a phospholipid and a polyethylene glycol, which comprises:
  a. dissolving said phospholipid and said polyethylene glycol in a solvent, thereby forming a solution;
  b. freezing the solution; and
  c. removing the solvent by lyophilization;
  wherein said polyethylene glycol has a percentage of folded polymeric chains of from 40% to 80%.

18. The method according to claim 17 wherein said phospholipid is DSPC, DPPG-Na or a mixture thereof.

19. The method according to claim 18 wherein said composition further comprises a fatty acid and said step a. comprises further dissolving said fatty acid in said solvent.

20. The method according to claim 19 wherein said composition comprises from 22 to 28 parts by weight of PEG4000, from 0.15 to 0.25 parts by weight of DSPC, from 0.15 to 0.25 parts by weight of DPPG-Na and from 0.02 to 0.06 parts by weight of palmitic acid.

21. A method for preparing a suspension of gas-filled microvesicles which comprises dispersing a freeze-dried powder composition according to claim 1, in the presence of a physiologically acceptable gas, in a physiologically acceptable liquid.

22. A method for preparing a suspension of gas-filled microvesicles which comprises dispersing a freeze-dried powder composition according to claim 11, in the presence of a physiologically acceptable gas, in a physiologically acceptable liquid.

23. The method according to claim 21 wherein said gas is sulfur hexafluoride.

24. The method according to claim 22 wherein said gas is sulfur hexafluoride.

* * * * *